United States Patent [19]

Cardinali et al.

[11] Patent Number: 5,021,600
[45] Date of Patent: Jun. 4, 1991

[54] NEW SILYLATING AGENT FOR THE PREPARATION OF CHROMATOGRAPHIC SUPPORTS

[75] Inventors: Franco Cardinali, Ostia Lido; Maria G. Longobardi, Rome; Giuseppe C. Viscomi, Monterotondo; Alessandra Ziggiotti, Colleverde Guidonia, all of Italy

[73] Assignees: Eniricerche S.p.A., Milan; Sclavo S.p.A., Siena, both of Italy

[21] Appl. No.: 393,787

[22] Filed: Aug. 15, 1989

[30] Foreign Application Priority Data

Sep. 2, 1988 [IT] Italy ................................ 21810 A/88

[51] Int. Cl.$^5$ .............................................. C07F 7/10
[52] U.S. Cl. ................................................... 556/411
[58] Field of Search ........................................... 556/411

[56] References Cited

U.S. PATENT DOCUMENTS

| | | | |
|---|---|---|---|
| 2,876,209 | 3/1959 | de Benneville et al. | 556/411 X |
| 4,059,559 | 11/1977 | Burkhardt et al. | 556/411 |
| 4,150,122 | 4/1979 | Sauers | 556/411 X |
| 4,360,517 | 11/1982 | Acker et al. | 556/411 X |

OTHER PUBLICATIONS

Journal of Organometallic Chemistry, vol. 99, 1975, pp. C1–C4, Siliciumorganische Verbindungen, Leonhard Birkofer et al.

*Primary Examiner*—Paul F. Shaver
*Attorney, Agent, or Firm*—Oblon, Spivak, McClelland, Maier & Neustadt

[57] ABSTRACT

A new mono-silylating agent of general formula (I)

$$(R_1,R_2,R_3)Si-NH-CO-O-Si(R_1,R_2,R_3) \qquad (I)$$

is described as well as its use in the preparation of chromatographic supports based on silica with functional groups covalently bonded thereto, the so-called "bonded stationary phases".

The new compounds are easy and safe to prepare from the coresponding mono-halosilanes with ammonium carbamate, and their use as silylating agents leads to stationary phases with a higher degree of surface coating than that attainable with the corresponding chlorosilanes.

4 Claims, No Drawings

NEW SILYLATING AGENT FOR THE PREPARATION OF CHROMATOGRAPHIC SUPPORTS

The present invention refers to new mono-silylating agents and to their use in the preparation of silica chromatographic supports with functional groups covalently bonded thereto.

Silica stationary phases with covalently bonded functional groups, generally called "bonded stationary phases", are the most commonly used packings in liquid chromatography.

They are widely used because of their efficiency and of the versatility of the functional groups which may be bonded thereto which make them suitable for a number of different separation and purification processes.

The use of silica as the inert support for this type of stationary phases is owed to the properties of this product, which can be summarized as follows: sufficient chemical inactivity; large surface area; wide possibility of selecting particle diameter (from 3 μm to 200 μm) and pore diameter (from 60 Å to 1000 Å); high mechanical stability to friction and pressure; commercial availability also in large amounts.

The reagents employed in the preparation of bonded-phases are organosilicon compounds wherein one or more of the silicon valences are activated by substitution with suitable chemical groups. Depending on the number of activated silicon valences, the silylating agents can be classified as mono-, di-, or tri-silylating agents.

Mono-silylating agents are those encompassed by the following general formula

wherein X is a leaving group such as Cl—, Br—, $H_2N$—, $(CH_3)_2N$—, $CF_3COO$—, HO—, $CH_3O$—, $CH_3$—$CH_2O$—; while $R_1$, $R_2$, and $R_3$ are alkyl residues containing from 1 to 22 carbon atoms, aryl residues, alkyl residues containing functional groups such as amino, hydroxy, cyano, and carboxy groups (Lork K. D., Unger K. K., Kinkel J. N., J.Chrom., 352, (1986), 199-211; Szabo K., Le Ha N., Zeltner P., Kovats E., Helv.Chim.Acta, 67. (1984), 2128-42).

Di- and tri-silylating agents are encompassed by the following general formulas

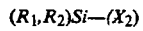

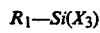

wherein, X, $R_1$, and $R_2$, have the same meanings as above.

All these silylating agents react with the free surface silanols on the silica to afford a siloxane bond. Different is however the stoichiometry of the reaction using mono-, di-, or tri-silylating agents.

In the case of mono-silylating agents the reaction scheme is the following one:

and the resulting stationary phases are monolayer. In the case of di- and tri-silylating agents, on the other hand, one or two silanols on the silica surface may react with the silylating agent to give the following species:

Di-silylating agents

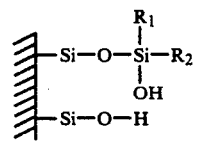 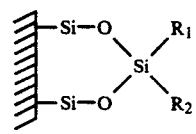

Tri-silylating agents

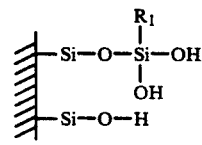 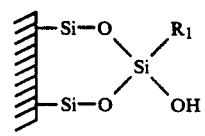

The Si—OH groups which form on the silica by hydrolysis of the reactant, may in their turn react with other silylating agent affording branched siloxane chains.

The main problem however of using di- and tri-silylating agents resides in the possible polymerization of a solution thereof in the presence of trace amounts of water, giving polysiloxane chains which then bond to the silica through the free Si—X functions.

The resulting stationary phases are named polymer phases.

In general, with an equal number of leaving groups X, di- and tri-silylating agents react with the silica silanols more rapidly and afford a denser coating layer on the silica surface than conventional monosilylating agents. Unfortunately, however, the lack of uniformity in the coating layer gives a poor reproducibility of the chromatographic characteristics cf the stationary phases obtained at different times.

As these drawbacks are not found in the preparation of monolayer stationary phases, the present trend is to use these last ones as chromatographic supports, using mono-silylating agents with the highest possible reactivity to afford acceptable coatings of the silica surface.

Among the compounds which may be used to this purpose, monochloro-trialkylsilanes are those most commonly employed because they are sufficiently reactive, cheap and easily available.

The evolution of hydrochloric acid, however, prevents reaction (1) proceeding to completeness. The addition of bases, which neutralise the acid formed, while increases completeness of the reaction (1)has a few disadvantages : the base should be added gradually in order to prevent an excess thereof causing damage to the silica and hydrolysing the just formed siloxane bonds; furthermore in situ salt formation may lead to high salt concentrations, mainly in the pores, with the risk of precipitations.

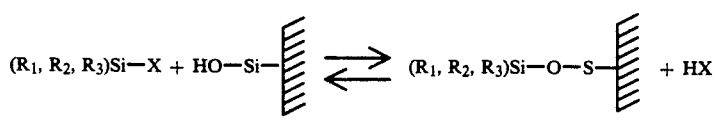

(1)

To overcome the problems generally involved with the formation of compounds of formula HX in reaction (1), the use of particular leaving groups (X=(CH$_3$)$_2$N—, H$_2$N—) has been proposed whose corresponding compounds HX (dimethylamine or ammonia) are volatile and can be withdrawn from the reaction environment by means of an inert gas stream (Szabo' K., Le Ha N., Zeltner P., Kovats E., Helv.-Chim.Acta, 67, (1984), 2128-42).

These compounds have a high silylating activity towards silica, but the serious problems which are involved in their synthesis, actually do not allow an industrial use thereof.

In synthesizing them, it is in fact necessary to work with liquid dimethylamine or liquid ammonia, and therefore at very low temperatures: said compounds are very reactive and it is necessary to set up particular measures to maintain anhydrous conditions; and, finally, both ammonia and dimethylamine are toxic products that—even more hazardous—are gas at room temperature.

It has now been found and represents a first object of the present invention, that it is possible to use as monosilylating agents for the preparation of bonded stationary phases, new N,O-bis-silylcarbamates, compounds which can be easily synthesized, which give a coating degree higher than that obtainable with the conventionally employed corresponding chlorosilanes. More particularly the new N,O-bis-silylcarbamates of the present invention have the following general formula (I)

(R$_1$,R$_2$,R$_3$)Si—NH—CO—O——Si(R$_1$,R$_2$,R$_3$)    (I)

wherein R$_1$ and R$_2$, each independently, represent a straight or branched alkyl radical containing from 1 to 22 carbon atoms, and R$_3$ represents a straight or branched alkyl radical containing from 4 to 22 carbon atoms, a straight or branched alkyl radical of from 1 to 22 carbon atoms substituted with one or more groups independently selected from amino, hydroxy, halogen, cyano, and carboxy, a mono- or poly-cyclic cycloalkyl radical of from 6 to 12 carbon atoms, a cycloalkyl-(C$_1$-C$_4$)alkyl radical, and a phenyl or naphthyl group optionally substituted with one or more (C$_1$-C$_4$)alkyl groups.

For the purposes of the present invention a preferred group of compounds of formula (I) comprises those compounds of formula (I) wherein R$_3$ is as defined above and R$_1$ and R$_2$, each independently, represent a straight or branched alkyl group of from 1 to 4 carbon atoms. A most preferred group of compounds comprises those compounds of formula (I) wherein R$_1$ and R$_2$, each independently, represent a straight or branched alkyl group of from 1 to 4 carbon atoms and R$_3$ is a straight or branched alkyl radical of from 4 to 22 carbon atoms, or a straight or branched alkyl radical of from 1 to 22 carbon atoms substituted as above. Some N,O-bis-silylcarbamates falling outside the above formula (I), and in particular N,O-bis-(trimethylsilyl)carbamate and N,O-bis(triethylsilyl)carbamate are known in literature as silylating agents for alcohols, phenols, and carboxylic acids (Birkofer L., Sommer P., J.Organomet.Chem., 99 (1975), C$_1$-C$_4$).

The compounds of the present invention can be easily synthesized starting from the corresponding halosilanes (typically chlorosilanes) and ammonium carbamate according to following reaction (2):

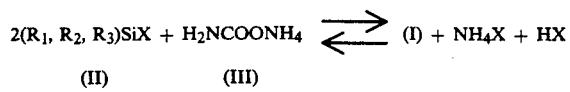

2(R$_1$, R$_2$, R$_3$)SiX + H$_2$NCOONH$_4$ ⇌ (I) + NH$_4$X + HX
(II)                (III)

wherein X is a halogen atom, typically chlorine

The reaction is carried out by contacting ammonium carbamate with an amount of halosilane (II) at least corresponding to the stoichiometric amount required by the reaction. It is generally preferred to use a slight excess of the halosilane (5-20 % by mol) even if it is possible and sometimes, when the reaction is carried out in not anhydrous conditions, is preferable to use a strong excess of halosilane (II).

The reaction is carried out in an a polar or polar aprotic, inert organic solvent, such as for example an optionally halogenated aliphatic or aromatic hydrocarbon, e.g. toluene, xylene, carbon tetrachloride, methylene chloride, dichloroethane, etc., a linear or cyclic ether, e.g. diisopropyl ether, tetrahydrofuran, and dioxane, dimethylsulfoxide, etc., in the presence of a molar amount of a non-nucleophilic base at least equal to the molar amount of the starting ammonium carbamate, to act as the acceptor of the hydrohalic acid which forms during the reaction. Suitable bases are the tertiary nitrogen containing organic bases, such as for example trialkylamines, e.g. triethylamine.

The reaction is carried out at a temperature of from about −10° C. to the reflux temperature of the reaction mixture. According to a preferred embodiment, the reactants are in fact contacted at a low temperature, preferably between −10° C. and +10° C., then the reaction course is speeded up by refluxing the reaction mixture. At the end of the reaction, which generally takes a few hours to be complete, the precipitate which forms is removed by filtration.

The resulting solution, which contains the desired compound of formula (I) may be employed as such in the preparation of the stationary phase or, if desired, compound (I) can be recovered therefrom by crystallization or precipitation by the addition of a non solvent.

The starting halosilanes of formula (II), and more particularly the chloro-silanes ((II):X=Cl) are commercially available products or they can be easily prepared according to methods known in literature or by simply adapting the methods known in literature to the particular substrate.

Said general methods, as an example, provides for the hydrosilylation of vinyl compounds with hexachloroplatinic acid as catalyst.

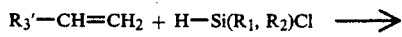

R$_3$'—CH=CH$_2$ + H—Si(R$_1$, R$_2$)Cl ⟶

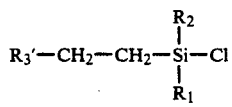

$$\begin{array}{c} R_2 \\ | \\ R_3'—CH_2—CH_2—Si—Cl \\ | \\ R_1 \end{array}$$

(see J. L. Speiser et al. in J.Am.Chem.Soc., 78, (1956), p.2278 et seq. and J.Am.Chem.Soc., 79, (1957), p.974 et seq.), or the reaction of a chlorodialkylsilane with a suitably selected Grignard reagent.

R$_3$MgBr + Cl(R$_1$, R$_2$)SiH ⟶ (R$_1$, R$_2$, R$_3$)SiH + MgBrCl

The silylation reaction for the preparation of the silica stationary phase with the new silylating agents of the present invention, proceeds with the following stoichiometry:

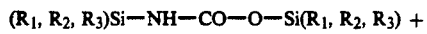
$(R_1, R_2, R_3)Si-NH-CO-O-Si(R_1, R_2, R_3) +$

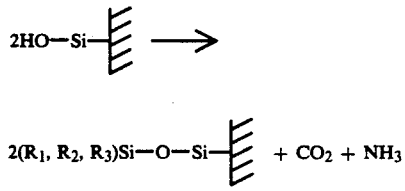

In order to have the maximum number of surface silanols (8,$\mu$mol/m$^2$), the starting silica is first hydrolysed with one or more mineral acids, as known in literature. Suitable acids are hydrochloric acid, sulphuric acid, nitric acid, and their mixtures (see for instance U.S. Pat. No. 4,324,689). Preferably however silica pretreatment will be carried out with diluted hydrochloric acid (Unger K. K., J.Chrom.Library, 16, (1979), pp.99-104).

The diameter of the particles of silica which can suitably be employed for the preparation of the bonded stationary phases, are not critical and may be as large as 150 $\mu$, even if, a diameter comprised between 5 and 50 $\mu$ is preferred.

The hydrolytic treatment is conveniently carried out at room temperature, then the silica is thoroughly washed with water up to neutral reaction, with an inert organic solvent miscible with water, typically a lower alkanol, e.g. methanol, ethanol, butanol, to remove the impregnation water, and finally dried.

The thus prepared silica is suspended in a polar aprotic or a polar, preferably high boiling, inert organic solvent, such as for instance toluene, xylenes, picolines, lutidines, etc.

Said solvent will preferably be dried before using it in order to avoid that trace amounts of water hydrolyse the silylating agent (I).

A number of equivalents of carbamate (I), which generally corresponds to 60-100 % of the total theoretical number of surface silanols as calculated from the surface area of the silica, is then added to the suspension. The suspension is then heated, generally to the reflux temperature, but in any case to a temperature lower than 200° C., and allowed to react for a few hours.

The reaction time needed will depend also on the temperature, as shorter reaction times are sufficient when higher temperatures are applied. Working however at 110°-120° C., generally 10-12 hours are sufficient.

The thus obtained functionalized silica is then recovered by filtration, washed a few times with a polar aprotic or apolar inert organic solvent, to remove traces of silylating agent (I), and optionally with a lower alkanol, typically, methanol, to remove possible impurities. After drying, the monolayer functionalized silica which is thus obtained can be used for the preparation of chromatographic columns or thin layer chromatographic supports.

Elemental analysis of the C-content of the thus obtained functionalised silica showed that the amount of carbon bonded is higher than that obtainable using other silylating agents such as the conventionally employed corresponding chlorosilanes.

The advantages of using the new compounds of formula (I) can thus be summarized as follows:in comparison to the corresponding chloroderivatives and in analogous preparation conditions, they afford stationary phases with a higher degree of coating; $CO_2$ and $NH_3$ evolve during silylation which are easily removed from the reaction environment with an inert gas stream; and can be easily synthesized starting from the corresponding chloroderivatives and ammonium carbamate.

The present invention is further illustrated in the following examples which however should not be interpreted as a limitation to the scopes thereof.

EXAMPLE 1

N,O-bis(dimethyloctadecylsilyl)carbamate

Ammonium carbamate (3.91 g, 50 mmol) is dissolved in anhydrous carbon tetrachloride (75 ml); the obtained solution is then cooled to 0° C., and a solution of dimethyloctadecylchlorosilane (36.44 g, 105 mmol) in carbon tetrachloride (20 ml) is then added thereto, followed by the addition of triethylamine (7.7 ml, 55 mmol).

The temperature is brought to 80° C. and the mixture is allowed to react for 4 hours.

The reaction mixture is then filtered under inert atmosphere and hexane is added to the filtrate to precipitate a compound which has been identified as the compound of the title both by $^{29}Si$ NMR spectroscopy (with two peaks characteristic of N,O-bis(trialkylsilyl)carbamates at 18.09 ppm [($R_1,R_2,R_3$)Si—O] and 3.357 ppm [($R_1,R_2,R_3$)Si—N]) and mass spectrometry (where, even if the molecular peak at 681 cannot be evidentiated, other diagnostic peaks can be found: m/e 666 (M+ —15) loss of a methyl group; m/e 428 (M+ —253) loss of a $CH_3(CH_2)_{17}$— group; m/e 356 corresponding to the following fragment:

$NH_2-COO-Si(CH_3,(CH_2)_{17}CH_3)$.

The recovered product (30.6 g, yield:90 %) is dissolved in anhydrous toluene (100 ml, 45 mM in carbamate) and kept under inert atmosphere.

EXAMPLE 2

Preparation of the bonded stationary phase

Lichrosorb ® Si—60 silica gel (5.0 g, 10 $\mu$, 60 Å, irregularly shaped, Merck) is suspended for 2 hours into 2M HCl (50 ml), is then washed with water up to neutral reaction and with methanol, and finally it is dried at room temperature for 12 hours and at 120° C. for further 12 hours.

A portion of the thus treated silica (4.5 g, 18 mmol of total silanols) is suspended in anhydrous toluene (70 ml) and anhydrous toluene 45 mM N,O-bis-dimethyloctadecylsilyl)carbamate (15.10 ml, 13.5 meq) is then added thereto.

The reaction mixture is kept under vacuum for 30 seconds and then refluxed for 12 hours.

The resulting silica is washed with toluene and methanol and dried at room temperature.

The elemental analysis showed that an amount of carbon of 15 %, corresponding to 1.5 ,$\mu$mol of aliphatic residues per m$^2$, was bonded to the silica.

Solid state $^{29}Si$ and $^{13}C$ cross polarization magic angle NMR spectroscopy (the peaks and their interpretation are reported below), confirms that the product is a monolayer phase (Bayer E., Albert K., Reiners J., Nieder M., J.Chrom., 264, (1983), 197–213.

$^{29}$Si (ppm): 12.90$_{(\equiv Si-O-R)}$; −101.68$_{(\equiv Si-OH)}$; −110.96$_{(\equiv Si-O-Si\equiv)}$.

$^{13}$C(ppm): −0.370$_{(1',1')}$; 13.019$_{(18)}$; 18.004$_{(1)}$; 23.190$_{(2,17)}$; 30.242$_{(4\div15)}$; 32.378$_{(16)}$; 33.974$_{(3)}$;

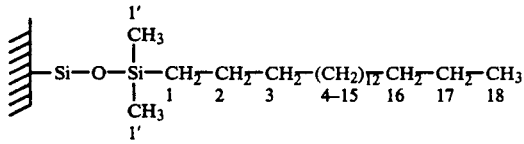

EXAMPLE 3

Packing of a chromatographic column

A 316 steel 150×4.6 column is packed at 8000psi with 2.1 g of the bonded stationary phase obtained in example 2, using 30 ml of methanol/glycerin (70/30, v/v) as the solvent to suspend the silica and isopropanol as the packing solvent.

The resulting column has 28000 plates/m.

COMPARATIVE EXAMPLE

By following substantially the same procedure as in example 2, but using 19.8 mmol of dimethyl-octadecyl-chlorosilane, instead of 13.5 meq of N,O-bis(dimethyloctadecylsilyl)carbamate, a bonded stationary phase is obtained with a C-content of 12.1 %, corresponding to 1.2,μmol of aliphatic residues per m$^2$.

What is claimed is:

1. A compound of general formula (I)

$(R_1,R_2,R_3)Si-NH-CO-O-Si(R_1,R_2,R_3)$      (I)

wherein $R_1$ and $R_2$, each independently, represent a straight or branched alkyl radical containing from 1 to 22 carbon atoms, and $R_3$ represents a straight or branched alkyl radical containing from 4 to 22 carbon atoms, a straight or branched alkyl radical of from 1 to 22 carbon atoms substituted with one or more groups independently selected from amino, hydroxy, halogen, cyano, and carboxy, a mono- or poly-cyclic cycloalkyl radical of from 6 to 12 carbon atoms, a cycloalkyl-($C_1$–$C_4$)alkyl radical, and a phenyl or naphthyl group optionally substituted with one or more ($C_1$–$C_4$)alkyl groups.

2. The compound of claim 1 wherein $R_1$ and $R_2$, each independently, represent a straight or branched alkyl group of from 1 to 4 carbon atoms.

3. The compound of claim 2 wherein $R_3$ is a straight or branched alkyl radical of from 4 to 22 carbon atoms, or a straight or branched alkyl radical of from 1 to 22 carbon atoms substituted with one or more groups independently selected from amino, hydroxy, halogen, cyano, and carboxy.

4. The compound of claim 3 which is N,O-bis-(dimethyloctadecylsily)carbamate.

* * * * *